United States Patent [19]

Gale

[11] Patent Number: 4,952,024
[45] Date of Patent: Aug. 28, 1990

[54] THREE-DIMENSIONAL SIGHT AND SOUND REPRODUCTION APPARATUS FOR INDIVIDUAL USE

[76] Inventor: Thomas S. Gale, 6 Ballater Court, Rexdale, Ont., Canada, M9V 3P3

[21] Appl. No.: 209,169

[22] Filed: Jun. 20, 1988

Related U.S. Application Data

[63] Continuation-in-part of Ser. No. 901,946, Aug. 29, 1986, abandoned.

[51] Int. Cl.$^5$ .............................................. G02B 27/22
[52] U.S. Cl. ...................................... 350/143; 358/88
[58] Field of Search ............... 350/130, 133, 134, 131, 350/132, 143, 145, 330; 351/158, 201; 358/88, 241

[56] References Cited

U.S. PATENT DOCUMENTS

| | | | |
|---|---|---|---|
| 2,955,156 | 10/1960 | Heilig | 358/88 |
| 2,966,550 | 12/1960 | Goldberg | 179/1 |
| 3,050,870 | 8/1962 | Heilig | 358/88 |
| 3,237,713 | 3/1966 | Leslie | 181/31 |
| 3,261,028 | 7/1966 | Coletta | 2/209 |
| 3,614,314 | 10/1971 | Rossire | 178/7.88 |
| 3,923,370 | 12/1975 | Mostrom | 350/55 |
| 3,969,583 | 7/1976 | Griese | 179/1 |
| 4,208,098 | 1/1978 | Johnson | 350/134 |
| 4,310,849 | 12/1982 | Glass | 358/88 |
| 4,395,731 | 7/1983 | Schoolman | 358/88 |
| 4,574,197 | 3/1986 | Kliever | 250/334 |
| 4,666,638 | 5/1987 | Baker | 261/26 |

FOREIGN PATENT DOCUMENTS 2113058 7/1983 United Kingdom ................. 358/88

OTHER PUBLICATIONS

"LVD for Flat TV Becomes a Reality" JEE, Feb. 1981 vol. 18, No. 170 pp. 90-92.

*Primary Examiner*—Rodney B. Bovernick
*Assistant Examiner*—Ronald M. Kachmarik
*Attorney, Agent, or Firm*—Rogers, Bereskin & Parr

[57] ABSTRACT

A three dimensional sight and sound reproduction apparatus for individual use is disclosed. The apparatus includes a headset having a central rib connecting an eye covering portion, a pair of depending lens and a rear portion. The eye covering portion substantially blocks ambient light from being viewed by the wearer of the headset and includes a first and second liquid crystal display screen spaced apart sideways. The images on the screens can be focused by use of lenses. Depending ear limbs are also provided containing a first and the second earphone adjacent to the ears of the wearer and being adjustable to suit the location of the individual wearer's ears. A rear portion is connectable to a plurality of signal sources including a first signal source for providing an image for the first liquid crystal display screen, a second signal source for providing an image for the second liquid crystal display screen, a third signal source for providing a sound for the first earphone and a fourth signal source for providing sound for the second earphone. The first and second signal sources are oriented to correspond to the spacing of human eyes and the third and fourth signal sources are oriented to sense sounds in a like manner to human ears.

11 Claims, 3 Drawing Sheets

THREE-DIMENSIONAL SIGHT AND SOUND REPRODUCTION APPARATUS FOR INDIVIDUAL USE

FIELD OF THE INVENTION

This is a continuation-in-part application from application Ser. No. 901,946, filed Aug. 29, 1986, now abandoned.

This invention relates to an apparatus of the type that is capable of reproducing three-dimensional sights and sounds for individual use. In particular, this invention relates to an apparatus that may be used to create a three-dimensional image, with three dimensional sound to enhance the reality and viewing pleasure of an individual using the apparatus.

BACKGROUND OF THE INVENTION

Two-dimensional viewing surfaces such as televisions or movie screens are well known and have been used extensively to provide entertainment. Moving images are displayed on the television screens or movie screens which depict some pre-recorded or live activity. However, such images are two dimensional and consequently the entertainment effect is somewhat limited in that the viewer is constantly aware that what is being seen and heard is a severely limited version of similar events in the real (three dimensional) world.

Attempts have been made in the past to provide a three dimensional image. One such attempt is to polarize a pair of images and then superimpose them upon each other. A viewer then wears a pair of glasses which allows only the appropriate image to be received by the appropriate eye. An analogous procedure is the use of red and green blocking lenses in glasses. However, while producing a three dimensional image, such approaches do not afford 3 D sound, or, more importantly the impression that what is being viewed is real. This is because the image, though 3-dimensional is like looking through a small window (the t.v. screen) across the room. Further, the image can be somewhat blurred and the eye strain caused by looking through such glasses often creates discomforts such as headaches. Therefore, an alternative means of producing a moving three-dimensional image with matched three-dimensional sound is desired.

Another alternative is to provide a stereoscopic television headset, such as is disclosed in U.S. Pat. No. 2,955,156 entitled STEREOSCOPIC-TELEVISION APPARATUS FOR INDIVIDUAL USE, which was granted on Oct. 4, 1960. In this apparatus, a pair of television tube units are adjustably mounted within a casing behind a pair of optical units. The optical units include inner and outer peripheral vision lenses. The casing has a pair of eye openings and may be strapped around an individual's head. In this manner the individual is able to see an individual image in each eye. Through use of appropriate signal sources, a visual three-dimensional effect can be achieved.

However, this prior invention has a number of difficulties and disadvantages. Firstly, the use of cathode ray tubes so close to the eyes is unacceptable to most viewers because of the perceived risk of radiation from the tubes. Further, the casing 10 is relatively large and awkward, and cannot be comfortably placed on the person seeking the three-dimensional image; a strap around the back of the head is required. Further, the earphones 27 are large and awkward. Because of its size, weight and awkward attachment, the viewer is constantly aware the device is being worn, which reduces the persuasiveness of the three-dimensional visual experience. A further, fundamental, limitation of this prior invention is its lack of a suitable sound signal source to complement the visual image. The sound is merely left-sight stereo—without the forward-backward, up-and-down characteristics of sound as naturally perceived.

BRIEF SUMMARY OF THE INVENTION

Accordingly, it is an object of the present invention to provide a three-dimensional image reproducing system which, by duplicating the aural and visual signals usually received by the brain of a viewer through the eyes and ears, creates an alternate reality in the mind of the viewer through the use of an apparatus that is easily adjustable and sufficiently light-weight to not distract the viewer. Therefore, according to one aspect of the invention there is provided a three-dimensional sight and sound reproduction apparatus for individual use comprising a headset having a center rib connecting a contoured eye-covering portion, a pair of depending ear limbs, and a rear portion, the eye-covering portion including adjustable means for substantially blocking ambient light from being viewed by the wearer of the headset, at least a first and a second liquid crystal display screen spaced at an interocular distance apart, on the same plane, and means for focusing any images displayed thereon; the depending ear limbs containing a first and a second means for reproducing sound adjacent the ears of the wearer of the headset, and means for adjusting the location of the first and second sound reproducing means to suit the individual wearer of the headset; the rear portion including means for connecting the headset, and thereby the liquid crystal display screens and the sound reproducing means, to a plurality of signal sources, including, a first signal source for providing an image for the first liquid crystal display screen; a second signal source for providing an image for the second liquid crystal display screen; a third signal source for providing a sound for the first sound reproduction means; a fourth signal source for providing a sound for the second sound reproduction means; said first and second signal sources being oriented to correspond to the spacing of a pair of human eyes, and said third and fourth signal sources being oriented to sense sounds in a like manner to human ears.

BRIEF SUMMARY OF THE DRAWINGS

The attached drawings show embodiments of the invention in which.

DETAIL DESCRIPTION OF THE PREFERRED EMBODIMENT

Figure 1:
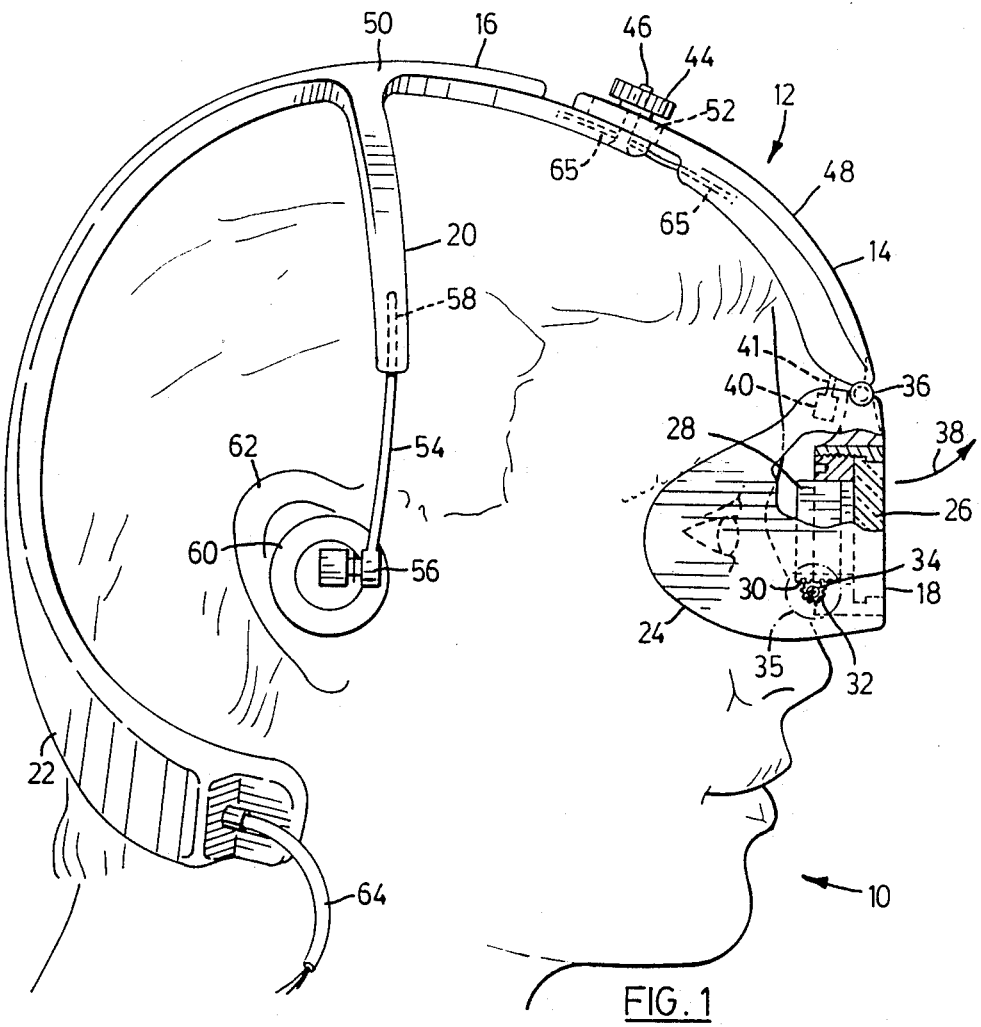
FIG. 1 is a side view showing the apparatus according to the present invention.

Referring to FIG. 1 is shown the head of an individual indicated generally at 10 wearing a three dimensional sight and sound reproduction apparatus indicated generally at 12. The apparatus 12 comprises a headset 14 having a center rib 16 connecting to a contoured eye covering portion 18. A pair of depending ear limbs 20 (only one of which is shown in FIG. 1) are provided, together with a rear portion 22.

The eye covering portion 18 includes a padded elastomeric rim 24 which essentially is a means for adjusting the eye covering portion 18 to substantially block ambient light from being viewed by the individual wearer 10. The rim 24 would preferably be porous and suitable for contacting the face of the wearer 10. A removable cover fabric may be provided, which could easily be cleaned. Also shown in the eye covering portion 18 is a liquid crystal display screen 26. It will be appreciated that although only one screen is shown in FIG. 1, there is provided a screen for each eye and the screens are spaced apart sideways to correspond with the spacing of the eyes of the viewer. In addition, a lens 28 is provided which enables the image on the screen 26 to be focused having regard to any perculiarities of sight of the wearer 10.

As shown in FIG. 1, the bottom of the lens 28 has a rack 30 formed therein and a pinion 32 is located on an axle 34. The axle 34 extends laterally out the side of the eye covering portion 18 and ends in a knob 35. The knob 35 is rotatable thereby rotating the pinion and moving the lens 28 in and out to enable the image on the LCD screen 26 to be focused.

Also shown in FIG. 1 is a hinge 36 which hingedly connects the eye-covering portion 18 to the center rib 16 of the headset 14. The hinge is preferably sufficiently stiff that the eye-covering portion 18 may be retained in position on the face of the viewer, or alternatively may be rotated upwards and retained in position out of the sight of the viewer, in the direction of arrow 38. In this manner, the apparatus can be easily adjusted to move the eye-covering portion 18, when the user desires a brief interlude from the subject matter being viewed. Detent means could also be provided to secure the eye-covering portion in either the raised or lowered positions. In addition, there is shown a plunger-type limit switch 40 which, when the eye-covering portion 18 is in the lowered position, connects an electrical circuit allowing the signals to be fed to the headset 14. However, when the eye-covering portion 18 is positioned in the raised position, a plunger 41 of the limit switch 40 extends, thereby breaking the electrical circuit and turning off the headset 14. It will now be appreciated that the limit switch 40 enables the viewer to be interrupted without necessarily losing place in the subject matter being viewed.

Also shown in FIG. 1 is a knob 44 which is attached to a post 46 on the upper part of the headset 14. The knob 44 is in fact threaded on the post 46 and together the knob 44 and the post 46 retain a front portion 48 of the headset to a rear portion 50. As can be seen, the post 46 is secured within the rear portion 50. The front portion 48 is provided with a slot 52, the ends of which are shown in dotted outline. By loosening the knob 44 the front portion 48 can be slid up and down thereby varying the height of the eye covering portion 18 in addition varying the size of the headset 14. In this manner, the headset is easily adjustable to the unique physiology of the individual viewer. By merely tightening the knob 44, the headset 14 can be fixed in position by securing the front portion 48 to the rear portion 50.

At the end of the depending ear limbs 20 are provided flexible tubes 54 which end in earphones 56. The flexible tubes 54 are housed within a tubular orifice 58 in the ear limbs 20. The tubes 54 are preferrably flexible, yet stiff enough to maintain a desired configuration. The tubes 54 may be slid vertically within the tubular orifice 58 to provide a height adjustment, and may be moved from front to back by bending the tube 54 to provide a front-to-back adjustment. In this manner the earphone 56 are sufficiently adjustable to accommodate the unique physiology of an individual wearer.

Also shown is an earphone pad 60 which is interposed between the wearer's ear 62 and the earphone 56. It will be appreciated by those skilled in the art that the earphone pad 60 may be of any elastomeric foam material having good sound transmitting properties, and would be preferably replaceable for hygenic reasons. Alternatively, the earphone pad 60 may be eliminated, leaving an inside-the-ear earphone preferred by some for its superior sound reproduction.

The centre rib 16 extends rearwardly around the head in a generally curved manner and terminates in a rear portion 22. When viewed from the rear, the rear portion 22 is in the shape of a curved upside-down T and the rear portion 22 generally conforms to the rear of the neck of the wearer. The rear portion 22 is preferably weighed slightly to balance the weight of the eye covering portion 18. Also, the rear portion 22 would preferrably have an elastomeric layer to increase the comfort of wearing the apparatus 10. Again, a removeable cover for washing could be provided.

Also shown is the wire 64 which provides the signal source inputs to the headset 14. Other wires, shown as 65, would be molded or otherwise placed into the headset 14, to transmit the signals, as required, from the wire 64, to both earphones 56, and both lenses 26.

Figure 2:
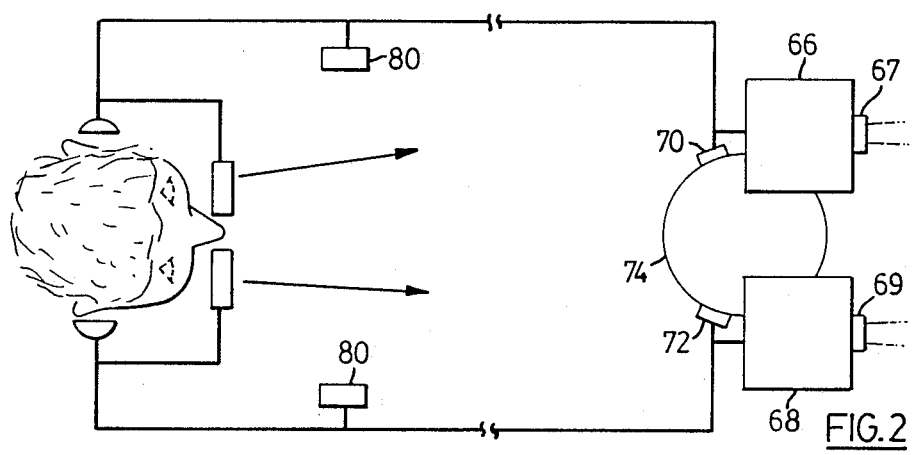
FIG. 2 is a schematic view illustrating signal sources for the embodiment of FIG. 1.

Turning now to FIG. 2, the signal source pattern for the headset can be understood. Essentially, the signal sources are an imitation of the sources which the head of the viewer might otherwise receive directly. Shown in FIG. 2 are a first camera 66 and a second camera 68 each having a respective lens 67 and 69. To provide the appropriate effect, the spacing of the lens 67 and 69 should be equivalent to the natural spacing of a pair of human eyes. Also shown are microphone soures 70 and 72 which have been located in or adjacent to the ear canals a simulated head 74. In this manner, the impression of three dimensional sound in addition to three dimensional sight can be created. The technique of creating three dimensional sound by placing microphones on opposed sides of a simulated head is taught in U.S. Pat. No. 3,969,583, which is incorporated herein by reference. Through the use of such three dimensional sound pick up and reproduction, the illusion of height, depth and distance in respect of the sounds can be maintained. This is not possible with simple left-right stereo systems.

As indicated above, liquid crystal display screens are used in the eye covering portion of the instant application. Conventional liquid crystal display screens have a pixel size of about 10 microns. However, this pixel size when viewed close up such as in the instant apparatus 12, creates a grainy image. Therefore, what is desired is a liquid crystal display screen having a pixel size of about three microns. The use of three or less microns for the pixel size will mean that the image will be reproduced in a manner that is closer to what the eye would see in real life. Further, while regular television, for example, is broadcast with 512 horizontal and vertical lines per image, the use of "high density t.v." signals would further enhance the image. In current high density t.v., there is provided 1,024 lines per image.

Liquid crystal display screens are also particularly suited for the instant application since they do not propogate radiation in the manner of a standard television tube. Further, they are lightweight and much less bulky than conventional television tubes, and therefore can be readily inserted into the eye covering portion 18 of the instant invention.

In a further enhancement of the replication of reality of the instant application, provision can be made for placing other sound signal sources 80 around the room. Thus, a low-frequency sub-sonic vibration could be provided to simulate the force of an explosion. In this manner, the body-shaking sensations could be reproduced in the viewer.

In addition to sight and sound, the present invention also relates to a scent system. The scent system provides for the release of specific scents, timed to the occurrence of events taking place in the subject matter being viewed. This is more particularly described below in relation to FIGS. 3 through 8.

Figure 3:
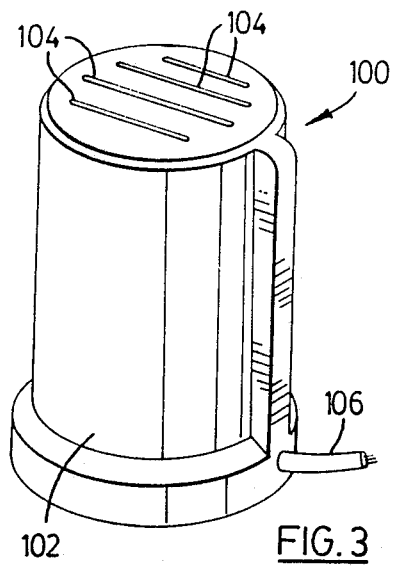
FIG. 3 is a scent source shown mounted on a table.

FIG. 3 shows a scent-producing device indicated generally at 100. In this particular embodiment, the device 100 is adapted to sit on any flat surface, such as a table or the like (not shown). The scent producing device 100 is comprised of an outer shell 102 which has a plurality of openings 104 to permit air flow into the interior of the outer shell 102. A wire 106 is shown, which electrically connects the device 100 to the apparatus 12, so that timed release of scents can be accomplished. Also, not shown, but described below, would be an exhaust opening in the outer shell 102.

Figure 4:
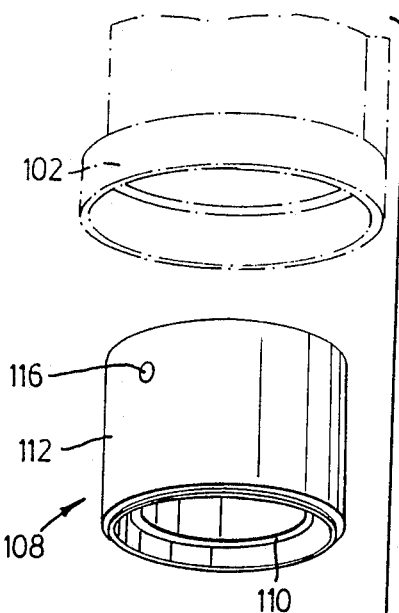
FIG. 4 is an exploded view of the scent source of FIG. 3.
Figure 4:
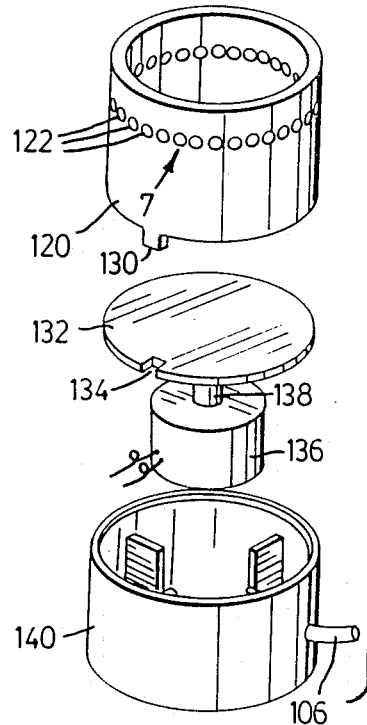

FIG. 4 shows the embodiment of FIG. 3 in exploded perspective. Shown in ghost outline at the top, is the outer shell 102. The next component shown is a stationary ring member 108 having inner wall 110, and outer wall 112. The inner wall 110 is attached to the outer wall 112 along the top, which is shown as 114 in FIG. 5. Also shown is an orifice 116. The orifice 116 extends through both inner and outer walls 110, 112, as shown in FIG. 5.

Figure 7:
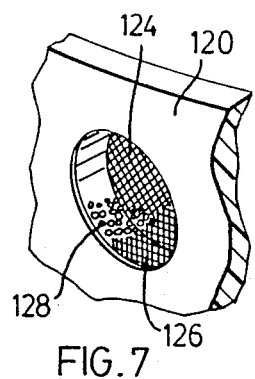
FIG. 7 is an enlarged perspective view along arrow 7 of FIG. 4.

The next component is a rotating scent ring 120. The scent ring 120 has a plurality of openings 122 each having a structure as shown in FIG. 7. For each opening 122 there is an inner screen 124 and an outer screen 126. Located therebetween are a plurality of scent pellets 128. The scent pellets in each particular opening 122 would have the same scent, but each opening 122 would have a different scent. In this manner, a large number of scents can be provided. At the lower end of the rotating scent ring 120 is provided a tab 130.

Below the ring 120 is located a revolving table 132. Formed into the revolving table 132 is a notch 134 to receive the tab 130. The revolving table 132 is driven by a motor, 136 having an axle 138. The motor 136 is preferrably a stepper motor, of the type that is capable of revolving a specific discreet amount. To complete the scent producing device 100, is shown the base 140.

Figure 5:
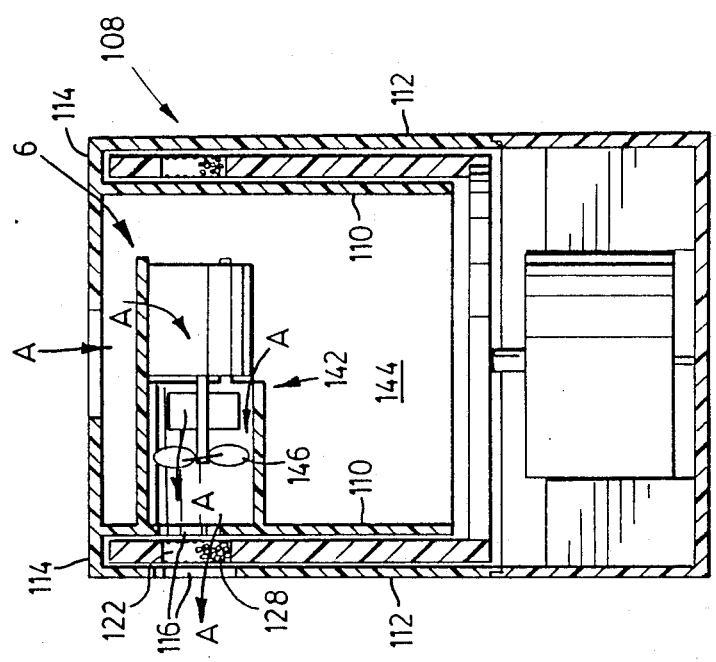
FIG. 5 is a vertical section through the scent source of FIGS. 3 and 4 with an outer cover removed.

Turning to FIG. 5, it can now be appreciated how the present device operates. Located on the inside of the stationary ring member 108 is a miniature motorized fan assembly 142. The fan assembly 142 is rigidly attached to the inner wall 110 as shown. Air is sucked into an inner chamber 144 and by reason of fan blades 146 the air is pushed out of the orifice 116. The passage of the air is indicated by arrows A. As can be seen in FIG. 5, as the air passes the scent pellets 128, located in opening 122, it will pick up a specific scent. It should be noted that the outer shell 102 is not shown in FIG. 5.

Figure 6:
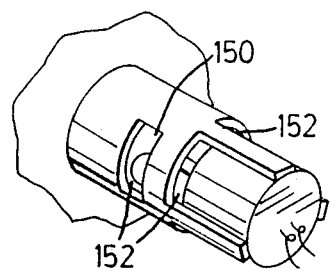
FIG. 6 is a part perspective view of a fan and motor assembly in the direction of arrow 6 of FIG. 5.

Upon a different scent being required, the stepper motor 136 is engaged and the rotating scent ring 120 is rotated to a new address. This exposes a different group of scent pellets 128 to the fan assembly 142 and the orifice 116. In this manner, any desired scent can be selected for a given image being viewed. As shown in FIG. 6 the air is allowed to pass into a fan chamber 150, by means of vents 152. When no scent is desired, the stepper motor returns to a home position, causing air to be blown through an openig 122 containing no scent pellets 128.

Figure 8:
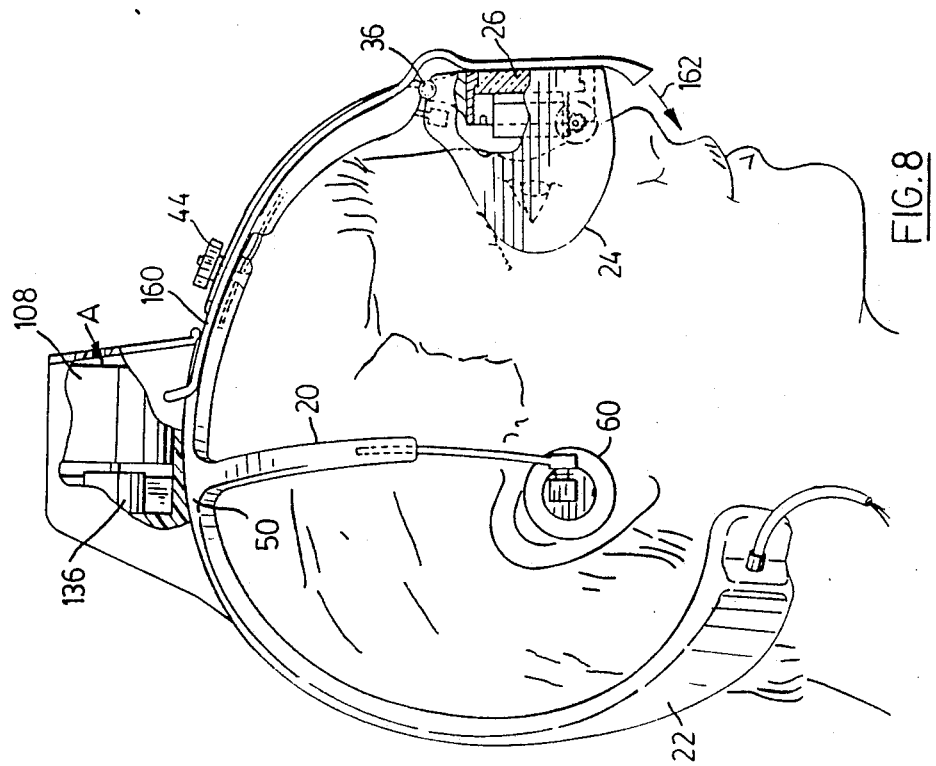
FIG. 8 is an alternate embodiment of the scent source shown mounted on the apparatus of FIG. 1.

Referring now to FIG. 8, an embodiment of the present scent apparatus is shown mounted on the apparatus 10. In this embodiment, like numerals refer to like components. The only real difference between this embodiment and the previous embodiment is that a tube 160 gathers the scent exiting from orifice 116 and through the exhaust opening in the outer shell 102 and carries it for discharge adjacent the nostrils of the person wearing the apparatus as shown by arrow 162.

From the foregoing, it will be apparent that many modifications and variations are possible within the broad scope of the present invention. Some of these modifications have been discussed above and others will be apparent to those skilled in the art.

I claim:

1. A three dimensional sight and sound reproduction apparatus for individual use comprising:
a balanced headset having a center rib connecting a contoured eye covering portion, a pair of depending ear limbs, and a rear portion,
the eye covering portion including adjustable means for substantially blocking ambient light from being seen by the wearer of the headset, at least a first and a second liquid crystal display screen spaced at an interocular distance apart on the same plane and means for focusing any images displayed thereon;
the depending ear limbs containing a first and a second means for reproducing sound adjacent the ears of the wearer of the headset, and means for adjusting the location of the first and second sound reproducing means to suit the individual wearer of the headset;
the rear portion including means for connecting the headset, and thereby the liquid crystal display screens and the sound reproducing means, to a plurality of signal sources, including,
a first signal source for providing an image for the first liquid crystal display screen;
a second signal source for providing an image for the second liquid crystal display screen;
a third signal source for providing a sound for the first sound reproduction means;
a forth signl source for providing a sound for the second sound reproduction means;
said first and second signal sources being oriented to and correspond to the spacing of a pair of human eyes, and said third and fourth signal sources being oriented to sense sounds in a like manner to human ears, the weight of the headset being generally balanced between the eye covering portion in the front and the rear portion, whereby the load of the headset is generally evenly distributed along said headset, wherein said rear portion includes a curved foot responsive to the wearer's neck to conform therewith, said foot including a weight to counterbalance the weight of the eye covering portion.

2. The invention of claim 1 wherein said headset further includes an aroma source said aroma source providing scents to correspond to the signal sources.

3. The invention of claim 2 wherein said aroma source comprises a stationary ring member having inner and outer walls, and an orifice formed in each of said inner and outer walls;
  a fan assembly mounted in said ring member said fan assembly directing air outward through said orifices;
  a rotating scent ring comprising a plurality of openings, each of said openings containing a specific scent source, and
  a motor for rotating said scent ring to align different of said openings to said orifices;
  whereby said scents may be altered to correspond with the audio-visual signal sources received.

4. The invention of claim 3 wherein said aroma source is adapted to rest on a surface generally adjacent the wearer of the headset.

5. The invention of claim 3 wherein said aroma source is mounted onto the headset and has a scent-conveying tube associated with said orifices to carry scent to a position in close proximity to the wearer's nostrils.

6. The invention of claim 1 wherein said eye covering portion is hingedly connected to said center rib, and may be maintained in an open position, or in a closed position.

7. The invention of claim 6 further including a switch to de-activate said headset upon the eye convering portion being placed in said open position.

8. The invention of claim 1 wherein said center rib includes a means for adjusting its length, the spacing between said eye covering portion and said rear portion being adjustable, responsive to the wearer's head size.

9. The invention of claim 1 wherein said sound reproducing means include replaceable ear insertion portions.

10. The invention of claim 1 wherein said adjustable means for substantially blocking ambient light from being viewed by the wearer of the headset comprises a substantially light impermiable foamed rim, responsive to the wearer's face to seal thereagainst.

11. The invention of claim 1 further including auxilliary sound reproducing means external to the headset and responsive to the signal sources.

* * * * *